United States Patent

Soltani-Ahmadi et al.

Patent Number: 5,554,796
Date of Patent: Sep. 10, 1996

[54] REMOVAL OF PRIMARY AND SECONDARY HYDROPEROXIDE IMPURITIES FROM TERTIARY HYDROPEROXIDES

[75] Inventors: Ahmad Soltani-Ahmadi, Radnor; Robert N. Cochran, West Chester, both of Pa.

[73] Assignee: ARCO Chemical Technology, L.P., Greenville, Del.

[21] Appl. No.: 235,823

[22] Filed: Apr. 29, 1994

[51] Int. Cl.$^6$ .................. C07C 409/00; B01D 3/34
[52] U.S. Cl. .................. 568/576; 203/37; 203/38
[58] Field of Search .................. 203/37, 38, 43, 203/36, DIG. 6; 568/576

[56] References Cited

U.S. PATENT DOCUMENTS

| | | | |
|---|---|---|---|
| 2,845,461 | 7/1958 | Winkler et al. | |
| 3,449,217 | 6/1969 | Harvey et al. | 203/6 |
| 3,864,216 | 2/1975 | Worrell et al. | 203/49 |
| 4,891,101 | 1/1990 | Sullivan | 203/36 |

FOREIGN PATENT DOCUMENTS

| | | |
|---|---|---|
| 0415572 | 3/1991 | European Pat. Off. . |
| 0431841 | 6/1991 | European Pat. Off. . |

OTHER PUBLICATIONS

CA 115: 8556.

*Primary Examiner*—Virginia Manoharan
*Attorney, Agent, or Firm*—William C. Long

[57] ABSTRACT

A process for the purification of tertiary alkyl hydroperoxide containing contaminating quantities of primary and secondary alkyl hydroperoxides by contacting the impure hydroperoxide mixture with anhydrous carboxylic acid derivative such as maleic anhydride and subsequently reacting the resulting mixture with basic material such as aqueous caustic and recovering purified tertiary alkyl hydroperoxide.

5 Claims, No Drawings

REMOVAL OF PRIMARY AND SECONDARY HYDROPEROXIDE IMPURITIES FROM TERTIARY HYDROPEROXIDES

BACKGROUND OF INVENTION

1. Field of the Invention

The present invention relates to the selective and efficient removal of primary and secondary hydroperoxide impurities from tertiary alkyl hydroperoxides which are produced by the oxidation of branched hydrocarbons. In particular, the primary and secondary hydroperoxide impurities are removed by contacting a mixture containing these impurities and tertiary alkyl hydroperoxide with a carboxylic acid derivative, preferably an anhydride such as maleic anhydride, in the absence of water, and thereafter reacting the resulting mixture with a base.

2. Description of the Prior Art

There a number of known methods for the removal of primary and secondary hydroperoxide impurities from tertiary hydroperoxides including distillation, thermal treatment, caustic treatment, and the like. These prior procedures, however, have definite disadvantages in that they are not sufficiently selective for the removal of the undesired impurities and require long reaction of residence times. The prior methods tend to destroy large amounts of the desired tertiary alkyl hydroperoxide during the purification process.

An especially pertinent patent in this area is U.S. Pat. No. 4,891,101 which shows a method for the removal of primary and secondary hydroperoxide impurities by contacting a tertiary alkyl hydroperoxide containing the impurities with a carboxylic acid derivative such as the anhydride and a basic compound such as sodium hydroxide. It is taught that approximately 80% of the primary and secondary hydroperoxides can be removed by the method shown in the patent. A disadvantage is that the process described requires large reactor sizes and results in a large consumption of the carboxylic acid derivative due to the fact that the reactions are conducted in the presence of a substantial excess of water. As a result, a significant amount of the acid anhydride reacts with the water to form acid which in turn reacts with alkali present to form salts. In fact, the state of the art is such that there exists room for improvement in the economies and efficiencies of the separation of primary and secondary hydroperoxides from tertiary alkyl hydroperoxides.

BRIEF DESCRIPTION OF THE INVENTION

The problems of the prior art are substantially overcome by contacting a mixture which is comprised of tertiary alkyl hydroperoxide, together with contaminating amounts of primary and secondary alkyl hydroperoxides, with a carboxylic acid anhydride such as maleic anhydride in the substantial absence of water and thereafter reacting the resulting mixture with a base. In this fashion, the concentration of contaminating primary and secondary hydroperoxides can be reduced by more than 90% while the amounts of acid anhydride employed can be greatly reduced as compared to prior procedures.

DETAILED DESCRIPTION OF THE INVENTION

In accordance with the present invention, a mixture comprised of tertiary alkyl hydroperoxide such as tertiary butyl hydroperoxide and also containing lesser amounts of primary and secondary hydroperoxides is purified. The hydroperoxide mixtures are conveniently obtained by molecular oxygen oxidation of the corresponding branched hydrocarbon in accordance with generally known conditions. The tertiary butyl hydroperoxide mixtures treated are those mixtures from isobutane oxidation after separation of unreacted isobutane.

In accordance with the invention, the impurities containing hydroperoxide mixture is first contacted with an anhydrous carboxylic acid derivative such as maleic anhydride. Although the derivative can be used as a solid, preferably the derivative is dissolved in a solvent such as tertiary butyl alcohol which is indigenous to the reaction system and this solution is admixed with the impure hydroperoxide mixture. Generally, it is preferred to carry out this mixing at moderate temperatures in the range of about 10°–40° C. for a sufficient time to insure thorough mixing of the materials. Illustrative mixing times are 1 second to about 1 hour, preferably 1 to 20 minutes. Higher temperatures can be employed, e.g. up to 150° C., but losses of tertiary alkyl hydroperoxide tend to increase at the higher temperatures.

Following the first contact of the impure hydroperoxide mixture and the carboxylic acid derivative, the resulting mixture is then reacted with a basic material such as aqueous sodium hydroxide. The absence of water during the first contact of the hydroperoxide with the carboxylic acid derivative enhances the utility of the derivative since there is essentially no reaction between the derivative and water which causes loss of derivative values to acid salts. The basic material, e.g. sodium hydroxide, is provided as an aqueous solution of the base. Reaction times of 1 second to 3 hours are suitable and temperatures of 10°–40° C. are preferred although higher temperatures, e.g. up to 150° C. can be employed for the reaction of the aqueous base with the acid derivative and impure hydroperoxide mixture. In this reaction the destruction of the primary and secondary alkyl hydroperoxides is completed and recoveries of purified tertiary alkyl hydroperoxide of the order of 90% or more are readily achieved.

Both the step of mixing with the acid derivative and of reaction with base are preferably carried out under an inert gas atmosphere. This provision is advantageous in avoiding formation of explosive mixtures since oxygen is released upon the primary and secondary hydroperoxide decomposition, and upon decomposition of any tertiary alkyl hydroperoxide.

Among the outstanding advantages of the present invention is the more efficient use of the acid derivative, the provision of smaller reaction zones thus enabling the process to be practiced with much less of a capital investment, and the enhanced removal of the primary and secondary hydroperoxides from the tertiary alkyl hydroperoxide.

The tertiary hydroperoxide to be purified in accordance with the process of the present invention may be any suitable organic hydroperoxide which does not possess a hydrogen attached to the same carbon as the hydroperoxide group. Examples of suitable tertiary hydroperoxides include tertiary amyl hydroperoxide and cumene hydroperoxide. Tertiary butyl hydroperoxide is a particularly preferred hydroperoxide and may be obtained by methods well known in the art. For example, liquid phase oxidation of isobutane with an oxygen-containing gas may be used to generate the tertiary butyl hydroperoxide as disclosed in U.S. Pat. No. 2,845,461. After removal of the unreacted isobutane, the crude oxidate recovered from the oxidizer is comprised of about 40 to 65 wt % tertiary butyl hydroperoxide, about 30 to 55 wt % tertiary butyl alcohol, and about 5 to 10 wt % of other oxidation by-products, including the primary and secondary hydroperoxides to be removed in accordance with the process of the invention. Generally the primary and secondary hydroperoxides are present in amount of 0.3 to 2.8 wt % based on the tertiary alkyl hydroperoxide.

The conventional process for recovering the desired tertiary butyl hydroperoxide product revealed in U.S. Pat. Nos. 3,449,217 and 3,864,216 requires neutralization of the isobutane free oxidate with base followed by distillation in the presence of a diluent vapor such as nitrogen. The tertiary butyl alcohol is removed, together with most of the low boiling oxidation byproducts, by azeotropic distillation with water. Azeotropic distillation is continued to obtain another fraction which contains the tertiary butyl hydroperoxide. The hydroperoxide fraction is subjected to further distillation to yield a composition containing 65 to 75 percent t-butyl hydroperoxide in water. These procedures can be followed after the treatment of the invention.

Any suitable carboxylic acid derivative can be used in the purification according to this invention, provided it does not contain a functional group with an acidic portion. Examples of suitable carboxylic acid derivatives include anhydrides, acid chlorides, esters, and amides. All of these carboxylic acid derivatives may react with the primary and secondary hydroperoxide impurities in the tertiary hydroperoxide to form peroxyester adducts. Acid anhydrides and acid chlorides are preferred due to their high reactivity. Anhydrides such as maleic anhydride and acetic anhydride are particularly preferred.

The amount of carboxylic acid derivative used in the process of this invention will depend on the concentration of the primary and secondary hydroperoxide impurities in the tertiary hydroperoxide product to be purified and the level of those impurities which is desired in the final product. Typically, about 0.1 to 5.0 milliequivalents of carboxylic acid derivative per gram of total hydroperoxide present is sufficient to reduce the concentration of the primary and secondary hydroperoxides by 90% or more.

It is preferred to use the base as an aqueous solution containing about 10–20 wt % base in water. The use of higher concentrations result in loss of tertiary alkyl hydroperoxide, while the use of lower concentrations reduces the effectiveness in removal of the primary and secondary alkyl hydroperoxide impurities.

Generally the use of about 1.0 to 20.0 milliequivalents of base per milliequivalent of carboxylic acid derivative is effective. Suitable basic compounds for use in the invention include strong bases such as alkali metal or alkaline earth hydroxides, and alkali metal or alkaline earth oxides as well as weaker bases such as alkali metal or alkaline earth carbonates, alkali metal or alkaline earth bicarbonates, and amines. Tertiary amines, including synthetic exchange resins containing tertiary amine functional groups, are preferred amines. Examples of particularly preferred basic compounds include potassium hydroxide and sodium hydroxide.

The following examples will serve to illustrate the practice of the present invention and the advantages which are achieved thereby.

An isobutane oxidate containing tertiary butyl hydroperoxide and tertiary butyl alcohol and containing minor, contaminating amounts of primary and secondary hydroperoxides in amount of 11.25 parts by weight is contacted with a solution of 0.49 part maleic anhydride in 1.41 parts of tertiary butyl alcohol. These materials are mixed at 30° C. for 20 minutes and then passed to a reaction zone where the mixture is contacted with 0.80 parts by weight sodium hydroxide in the form of a 15% aqueous solution. Reaction conditions in this reaction zone are a temperature of 30° C. and a residence time of 15 minutes.

As a result of the treatment as above described, 93% of the primary and secondary contaminating hydroperoxides are converted into non-peroxidic materials and are conveniently separated from the tertiary alkyl hydroperoxide product mixture.

When this practice is contrasted with procedures such as those described in U.S. Pat. No. 4,891,101, will be seen that almost half the maleic anhydride is needed, considerably less than half of the aqueous caustic is needed, and a far greater percentage of the primary and secondary alkyl hydroperoxides is effectively removed by the process of this invention.

We claim:

1. A process for purification of tertiary alkyl hydroperoxide which contains contaminating amounts of primary and secondary alkyl hydroperoxides to reduce the content of said primary and secondary alkyl hydroperoxides which consists essentially of admixing the tertiary alkyl hydroperoxide with a carboxylic acid derivative under substantially anhydrous conditions at 10°–150° C. for 1 second to 1 hour, subsequently reacting the resulting admixture with a base at 10°–150° C. for 1 second to 3 hours, and recovering tertiary alkyl hydroperoxide reduced by at least 90% in the content of primary and secondary alkyl hydroperoxides.

2. The process of claim 1 wherein the tertiary alkyl hydroperoxide is tertiary butyl hydroperoxide.

3. The process of claim 1 wherein the tertiary alkyl hydroperoxide is tertiary amyl hydroperoxide.

4. The process of claim 1 wherein the carboxylic acid derivative is maleic anhydride.

5. The process of claim 1 wherein the base is sodium hydroxide.

* * * * *